(12) United States Patent
Fries et al.

(10) Patent No.: US 6,292,919 B1
(45) Date of Patent: Sep. 18, 2001

(54) METHODS AND APPARATUS FOR EXCHANGING DATA IN AN IMAGING SYSTEM

(75) Inventors: Mark David Fries, Williams Bay; Phil E. Pearson, Jr., Waukesha, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/139,546

(22) Filed: Aug. 25, 1998

(51) Int. Cl.[7] .................................................. G06F 11/10
(52) U.S. Cl. ............................................ 714/758; 714/746
(58) Field of Search .................................... 714/758, 746, 714/807

(56) References Cited

U.S. PATENT DOCUMENTS

| | | |
|---|---|---|
| 5,134,639 | 7/1992 | Vekstein et al. . |
| 5,212,737 | 5/1993 | Ackelsberg . |
| 5,229,871 | 7/1993 | Czarnek et al. . |
| 5,287,117 | 2/1994 | Posluszny . |
| 5,596,437 | 1/1997 | Heins . |
| 5,910,182 | * 6/1999 | Dent et al. ............................ 714/786 |
| 6,044,485 | * 3/2000 | Dent et al. ............................ 714/774 |

OTHER PUBLICATIONS

PCI Local Bus specification, Revision 2.1, effective Jun. 1, 1995, available from PCI Special Interest Group, Portland, OR. Total of 9 pages from chapters 1, 2, and 3.

* cited by examiner

Primary Examiner—Phung M. Chung
(74) Attorney, Agent, or Firm—Armstrong Teasdale LLP; Christian G. Cabou

(57) ABSTRACT

The present invention, in one form, is a communication system for transmitting high-speed data across an imaging system slip-ring. In one embodiment, the communication system includes a transmitter and a receiver. The transmitter generates encoded serial data that is transmitted across the slip-ring 1 bit at a time to the receiver. The encoded data includes command codes, message blocks having CRC data, and SYNC data. Using the commands codes, the receiver decodes the data into byte data. The receiver utilizes the CRC data to detect and correct errors in the transmitted data and the SYNC data to synchronize the receiver with the transmitter.

28 Claims, 6 Drawing Sheets

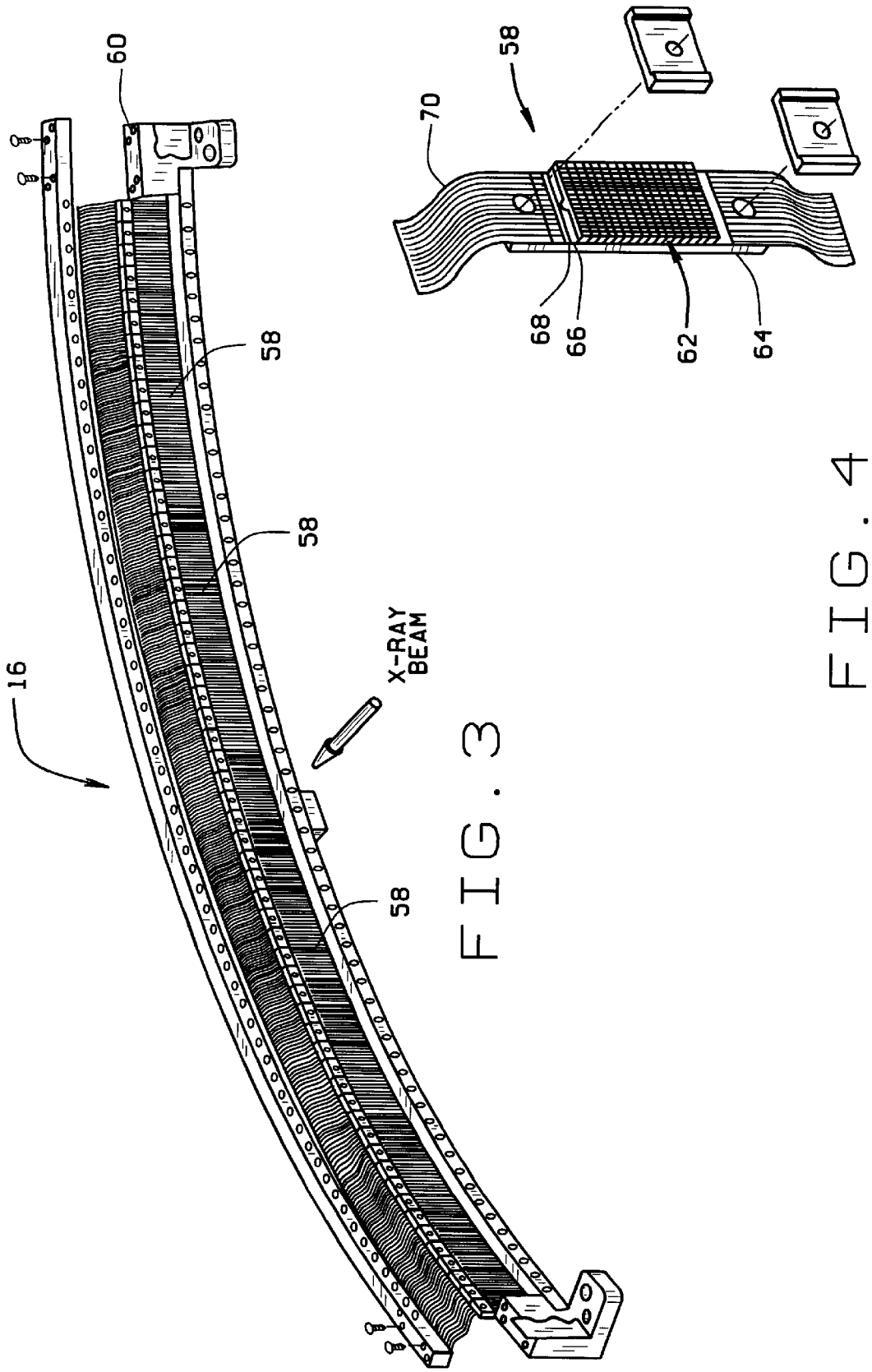

METHODS AND APPARATUS FOR EXCHANGING DATA IN AN IMAGING SYSTEM

BACKGROUND OF THE INVENTION

This invention relates generally to data communications and, more particularly, to exchanging data in an imaging system In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view ". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

At least one known CT imaging system sends imaging data collected by the detector array across a slip-ring having a shoe and a copper ring mechanism at a rate of about 1.5 megabytes (MB) per second during normal scanning. A receiver of the imaging data checks the data and, if the data is correct, sends an acknowledgment to a transmitter that the correct imaging data was received. Using this method, the slip-ring has the capability of transmitting data at about 5.0 MB per second, and uses the excess bandwidth for re-transmission of the imaging data in the event of an error. However, as scan speeds are increased and additional data is collected in the detector array, data must be transmitted over the slip-ring at a faster rate. As a result, there is insufficient bandwidth to provide a communication path back from the receiver of the imaging data to the transmitter. In addition, because corrected data must be re-transmitted when an error occurs, scanning speeds are limited.

To increase the rate of data transfer within the imaging system, it is desirable to provide communication system, or circuit, which transmit data without requiring an acknowledgment be sent from the receiver to the transmitter. It would also be desirable to provide such a circuit which corrects data errors without re-transmitting the imaging data.

BRIEF SUMMARY OF THE INVENTION

These and other objects may be attained by an imaging system which, in one embodiment, includes a communication system, or circuit, transmits imaging, or CT, data from a data acquisition system to a computer or image reconstructor. The communication system includes a transmitter for encoding and transmitting the imaging data and a receiver for receiving and decoding the imaging data.

In one aspect, the present invention is directed to transmitting imaging data across a slip-ring at a high rate of speed without transmitting information from the receiver to the transmitter. More specifically, the transmitter receives parallel data from the data acquisition system and converts the parallel byte data into a serial stream of data. The serial data is transmitted across the slip-ring 1 bit at a time to the receiver. The receiver then decodes the serial data into parallel byte data. More specifically, the encoded data includes command codes, message blocks, and SYNC data. The command codes include data so that the receiver starts decoding the serial data at the proper time. The message data includes the imaging data and Cyclic Redundancy Check (CRC) data representative of the transmitted imaging data. The CRC data is utilized by the receiver to detect and correct errors in the transmitted imaging data. The SYNC data is utilized to synchronize the receiver with the transmitter.

The above described imaging system communication circuit transmits high-speed data across an imaging system slip-ring without requiring an acknowledgment be sent from the receiver to the transmitter. In addition, the communication circuit corrects data errors without re-transmitting the data.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Figure 1:
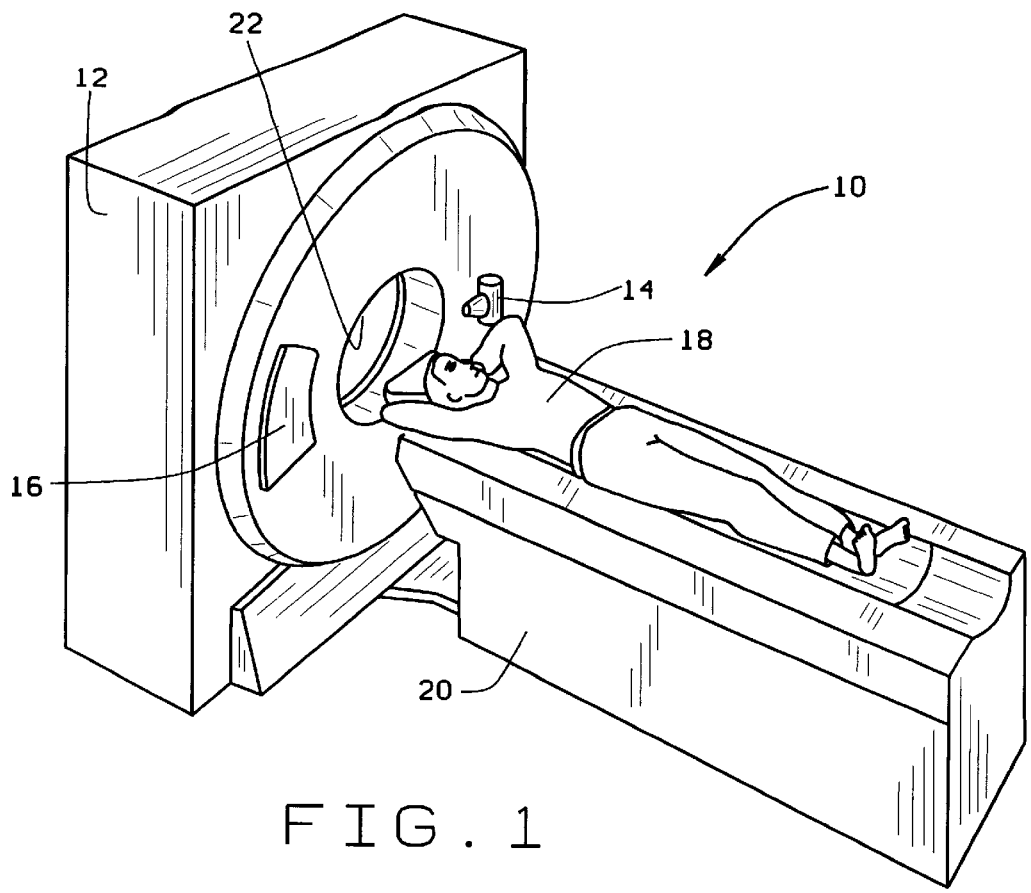
FIG. 1 is a pictorial view of a CT imaging system.

Referring to FIG. 1, a computed tomography (CT) imaging system 10 in accordance with one embodiment of the present invention is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
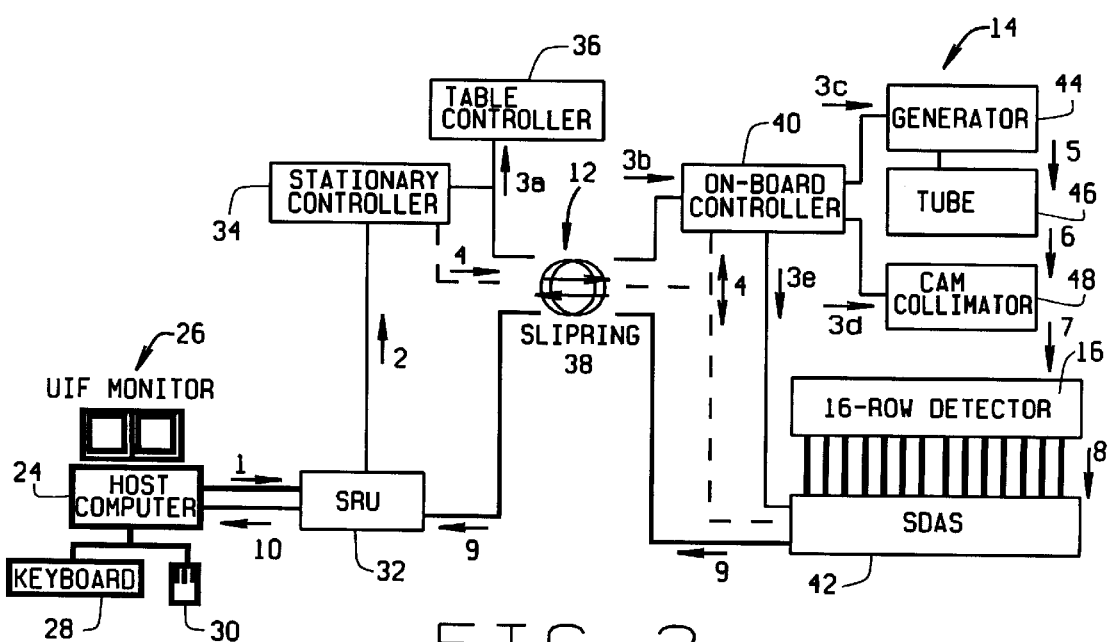
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor (user interface) 26 for displaying images and messages to an operator. Computer 24 also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction digital signal processing board for performing preprocessing, which is known in the art. SRU 32 further includes an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. Slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card and 1408 Hz sampling can be performed. SDAS 42 also includes a front-end pre-amplifier for amplifying the signals. Further details regarding SDAS are set forth below.

On-board controller 40 controls operation of x-ray source 14 and operation of SDAS 42. X-ray source 14 includes a high voltage generator 44 coupled to an x-ray tube 46. Tube 46 may, for example, be the tube known in the art as the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

In FIG. 2, data flow is illustrated by bold lines, control flow is illustrated by normal lines, and real-time control flow is illustrated by dotted lines. The numeric identifiers associated with the flows are set forth below.
  1: scan and reconstruction prescription from operator
  2: scan prescription to "master" controller
  3: scan parameters distributed
    3a: table position
    3b: rotating parameters
    3c: kV and mA selections
    3d: x-ray beam collimation and filter selections
    3e: detector slice thickness and SDAS gain selections
  4: real-time control signals during scanning
  5: high voltage
  6: un-collimated x-ray beam
  7: collimated x-ray beam
  8: analog scan data
  9: digital scan data
  10: patient images Rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

As shown in FIGS. 3 and 4, detector array 16 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and SDAS 42. Particularly, each switch apparatus FET input is electrically connected to a photodiode array output and each switch apparatus FET output is electrically connected to SDAS 42, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 24. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system SDAS 42. In one embodiment defined as a 16 slice mode, decoder 68 enables switch apparatus 66 so that all rows of the photodiode array are electrically connected to SDAS 42, resulting in 16 separate, simultaneous slices of data being sent to SDAS 42. Of course, many other slice combinations are possible.

In one specific embodiment, detector 16 includes fifty-seven detector modules 58. The semiconductor array and scintillator array 62 each have an array size of 16×16. As a result, detector 16 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 16 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
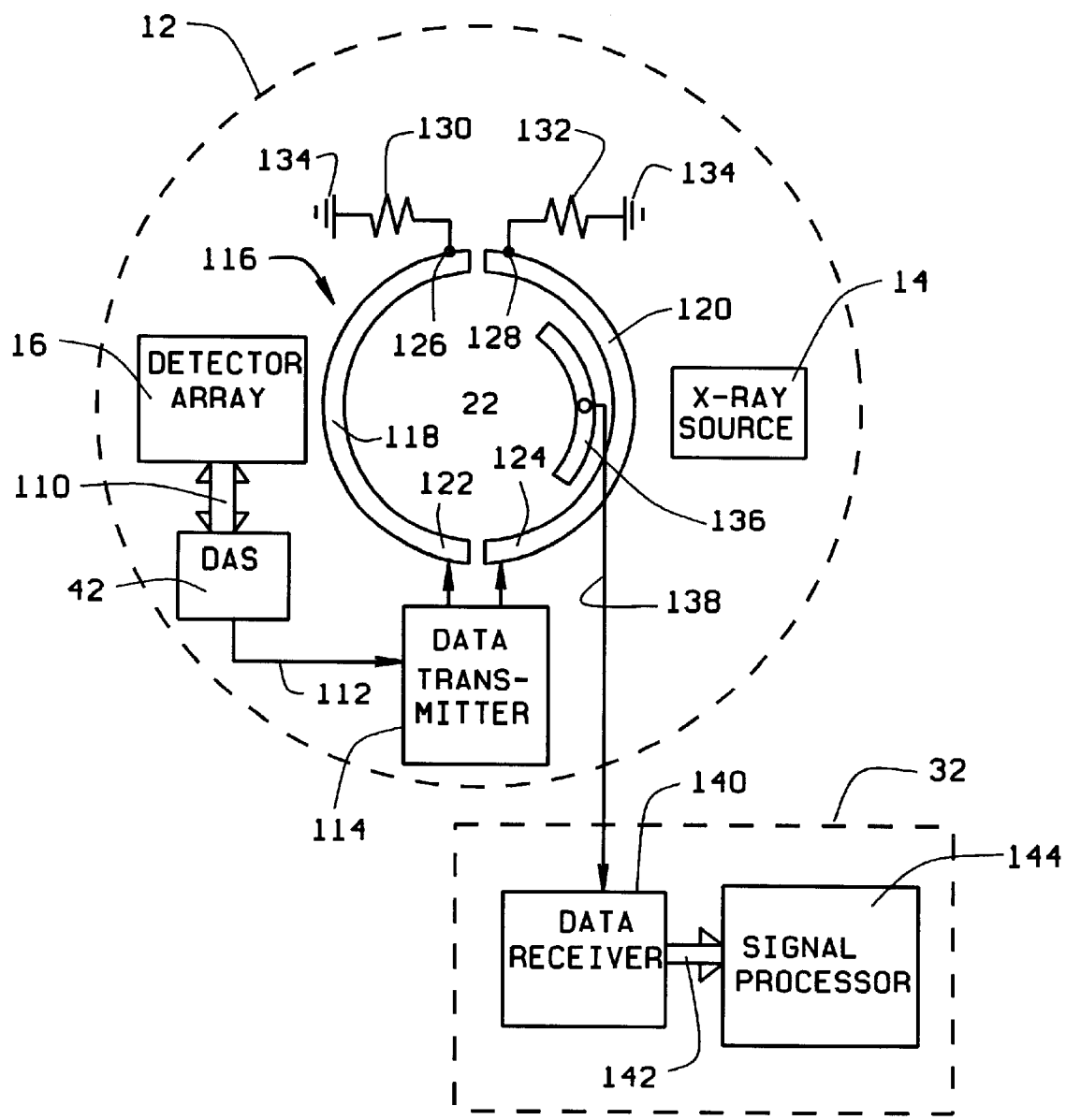
FIG. 5 is a block diagram of the slip ring.

Referring now to FIG. 5, which is a simplified, figurative schematic block diagram of gantry 12. The signals from detector array 16 are provided through lines 110 to data acquisition system (SDAS) 42, which converts each signal from an analog signal format into digital data, typically, two bytes having 16 bits. The digital data is provided on lines 112 to a data transmitter 114 disposed on gantry 12. Data transmitter 114 digitally encodes the data with an RF (radio frequency) pulse pattern, and the RF encoded signal is presented to an electromagnetic coupler, such as an RF slip ring 116 of the type disclosed in U.S. Pat. No. 5,530,424 to Harrison et al, which is assigned to the assignee of this application and which is incorporated by reference herein.

The '424 RF slip ring configuration includes one or more transmission lines disposed on the rotating side of the interface; one coupler segment mounted on the relatively stationary side. Depending on the distance between the stationary coupler and the rotating transmission line, a number of transmission line segments may be required to ensure that the coupler is always in spatial proximity to at least one of the segments to receive the electromagnetic signal. In that case each segment has a length which is a fractional portion of the arc length of the gantry's rotational path. The segments are cascaded, end-to-end around the gantry's rotational axis, typically along the circumference of the aperture 22 such that the aggregate length provides a substantially 360° arc, i.e. a full rotation of the gantry.

Two transmission line segments 118, 120 are used and are mounted in a manner to provide adjacent positioning of first ends 122, 124 and second ends 126, 128 of transmission lines 118, 120, respectively. Contiguous placement of the ends of each of the transmission lines provides substantial continuity of the electromagnetic coupling along the full rotational path of the gantry.

Data transmitter 114 provides the encoded data to first ends 122, 124 of each of the transmission lines 118, 120. Second ends 126, 128 of each transmission line are connected through terminal impedance's 130, 132 to signal ground 134. A coupler element 136 positioned on the stationery frame in a manner to ensure physical proximity of the coupler to one and both of the transmission lines 118, 120 during gantry rotation. The encoded data is electromagnetically coupled through to coupler 136, as described in the hereinbefore incorporated '424 patent to Harrison et al.

On the stationery frame side, the coupled data signal is provided on a line 138 to SRU 32. The encoded data is received at a data signal receiver 140. As described in detail hereinafter with respect to FIG. 6, signal receiver 140 decodes the serial data using a Forward Error Correction (FEC) algorithm and provides the decoded data through lines 142 to a signal processor 144. Signal processor 144 includes signal memory (not shown) for storing the program algorithms which govern the CT processing of the received data in response to operator commands. Signal processor 144 collates the decoded imaging data sets into a composite view associated with the particular angular position of the gantry.

Figure 6:
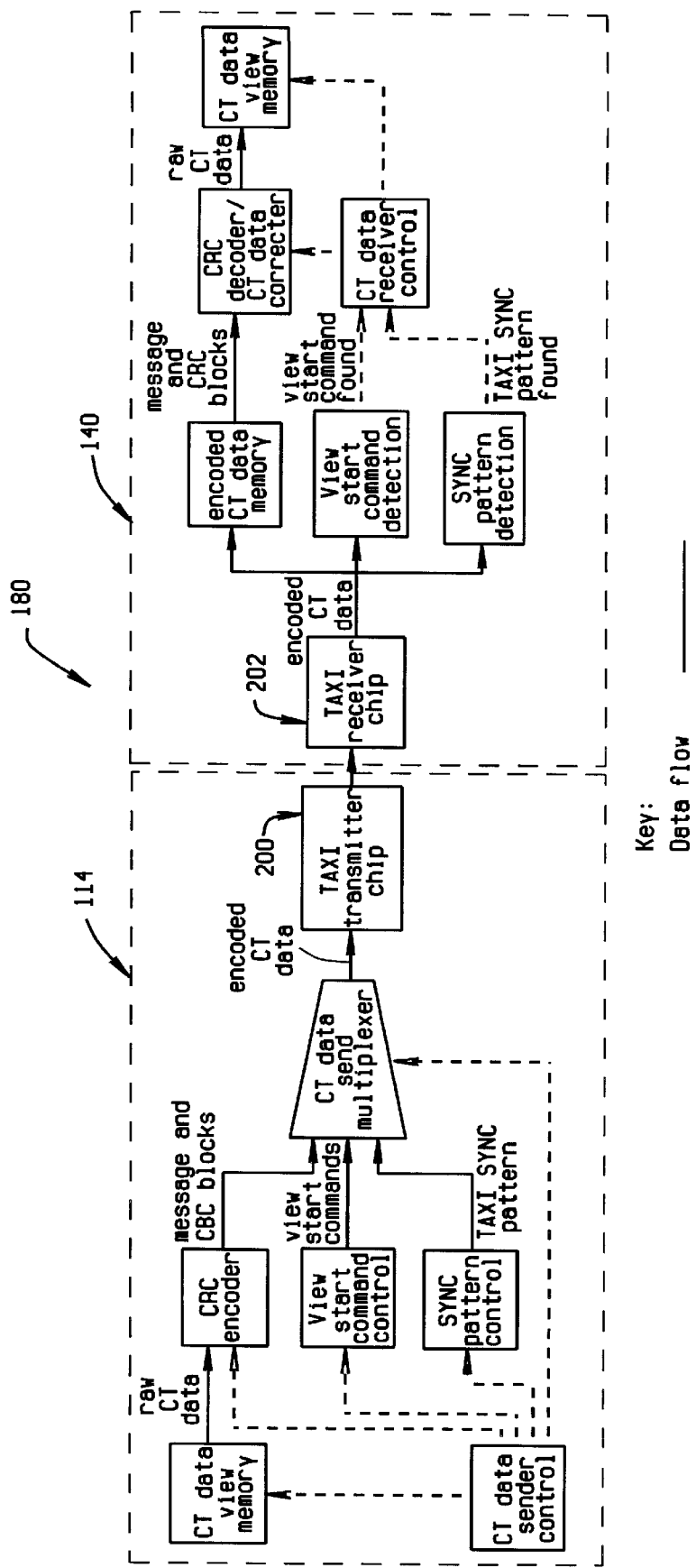
FIG. 6 is a block diagram of a communication system in accordance with one embodiment of the present invention.

Referring now to FIG. 6, a communication system, or circuit, 180, includes transmitter 114 and receiver 140 utilizing the FEC algorithm to transmit high speed data from DAS 42 to SRU 32. More specifically and in one embodiment, transmitter 114 encodes the data from DAS 42 utilizing a FEC transmitter 184 and a Transparent Asynchronous Transmitter/Receiver Interface (TAXI) transmitter 200 and receiver 140 decodes the data transmitted from transmitter 114 through slip-ring 116 utilizing a TAXI receiver 202 and a FEC receiver 204. For example, TAXI transmitter 200 is an Advanced Micro Devices, Inc. (AMD), part no. AMD7968-125JC and TAXI receiver 202 is also manufactured by AMD, part no. AMD7969-125JC. Particularly, TAXI transmitter 200 receives parallel data from DAS 42 and encodes the parallel data in to a serial bit stream, for example, a 10 bit serial stream. The serial bit stream, or data, is then transmitted across slip-ring 116, one bit at a time. TAXI receiver 202 receives the serial bit stream from slip-ring 116 and decodes the serial bit stream into a data byte. The data byte is then verified and, if required, corrected.

More specifically and in one embodiment, TAXI transmitter 200 is a byte-in-serial-out device and TAXI receiver 202 is a serial-in-byte-out device. A byte of imaging data is encoded into a 10-bit serial stream, via a 4B/5B (4 byte then 5 byte) method and the encoded data is transmitted with a Non Return to Zero, Invert on One (NRZI) standard protocol. Receiver 202 is configured to only receive data from transmitter 200 and does not provide an acknowledgment or verification to transmitter 200 of receiving correct data. A Phase Lock Loop (PLL) (not shown) within transmitter 200 is utilized to synchronize transmitter 200 and receiver 202. The PLL imbeds a clock in the NRZI bit pattern. Utilizing transmitter 200 and the 4B/5B encoding of the imaging data, a maximum number of edges are placed in the serial bit stream so that TAXI receiver 202 can recover the transmitted clock and synchronize with transmitter 200. During periods when no imaging data is being transmitted, TAXI transmitter 200 is configured to automatically send a special pattern of 1's and 0's, called a SYNC pattern, to receiver 202. The SYNC pattern, or data, provides a serial stream of data having edges needed to keep TAXI receiver 202 in phase lock with TAXI transmitter 200 and provides byte synchronization between TAXI transmitter 200 and TAXI receiver 202.

More specifically, the encoded data from transmitter 200 includes command codes, data blocks, and SYNC data where the data from DAS 42 includes at least one data view. Particularly, transmitter 200 utilizes TAXI codes, or command codes, to send a signal, or data, to receiver 202 indicating a start of an imaging data view. Transmitter 200 then divides each data view into blocks of data, called message blocks, and appends a Cyclic Redundancy Check (CRC) to each message block. The CRC is a mathematical description of the data in the corresponding message block. Transmitter 200 also generates, or inserts, a TAXI SYNC bit sequence, or data after a defined, or selected number of message blocks.

TAXI receiver 202 includes a count-to-10 counter that shifts in a defined number of bits, for example 10 bits, and then decodes the bit pattern into the data byte transmitted from TAXI transmitter 200. In addition, TAXI receiver 202 includes byte synchronization logic (not shown) to stop receiver 202 from receiving of data every selected number of bytes, where the selected number of bytes is the same as the selected number of bytes in transmitter 200, to determine whether a SYNC pattern follows a shifted in serial bit. Incoming data into receiver 202 is initially examined to determine, or detect, whether the data includes a sequence of TAXI command codes, for example, to determine the start of a data view. The command codes prevent noise generated by, for example slip-ring 116, from falsely starting receiver 202 in decoding the transmitted data. After receiving the proper command code, receiver 202 receives message blocks and CRC blocks. After separating the message blocks and the CRC blocks, receiver 202 determines a received CRC block, or data, for the received data, utilizing the CRC algorithm discussed hereinafter.

The received CRC block is then compared to the transmitted CRC block to determine if a transmission error occurred. If a transmission error has occurred, the transmitted CRC block is utilized to correct the error containing received message block. After completing the transmission of view data, transmitter 200 transmits the SYNC bit sequence to receiver 202 to maintain synchronization of transmitter 200 and receiver 202. The SYNC bit sequence is utilized by receiver 202 to determine a starting bit position of a transmitted imaging data byte.

Described below, in more detail, are algorithms for performing the above described functions. More specifically and in one embodiment, transmitter 200 and receiver 202 utilize a CRC Encoding/Decoding algorithm and a View Start Detection algorithm.

CRC Encoding/Decoding Algorithm

The CRC encoding and decoding protocol, within communication system 180, specifically, transmitter 184 and receiver 204, detects and corrects the types of errors commonly encountered during data transmission using slip-ring 116. These types of errors, typically, include random errors of a single bit error occurring every $10^{12}$ bits and burst errors that are caused by system noise events, for example, electrostatic discharge or tube spits. Burst errors typically occur more frequently than random errors and have a longer duration. The duration of the burst errors, however, are typically bounded to less than 300 nanoseconds (nS) and do not occur more often than every 25 microseconds (uS).

Figure 7:
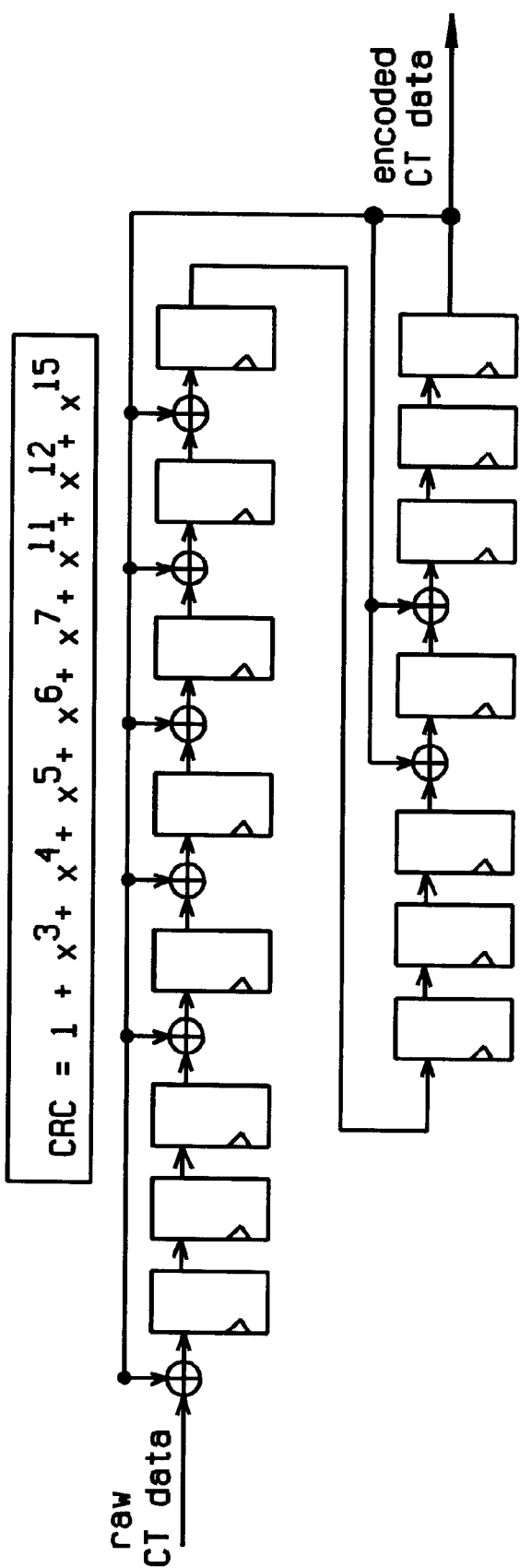
FIG. 7 is a exemplarary CRC circuit.

Transmitter 184 and receiver 204 correct for burst errors by utilizing a burst specific CRC algorithm. In one embodiment, the burst specific CRC code, or data, includes a message block length of 136 data bytes and a CRC block length of 15 bytes so that a burst error of 6 bytes long or less, for example 550 nS (6 bytes*91 nS/byte), is detected and corrected in receiver 202. By utilizing a message block length of 136 bytes, receiver 204 is configured to detect and correct a burst error every 15 uS ((136+15)bytes*91 nS/byte). An exemplary CRC circuit representing the CRC algorithm is shown in FIG. 7. A similar CRC algorithm and circuit implementation is used for receiver 204. In addition, however, receiver 204 includes a comparison circuit (not shown) to compare the received data CRC to the transmitted CRC to detect errors in the message data.

View Start Detection

Figure 8:
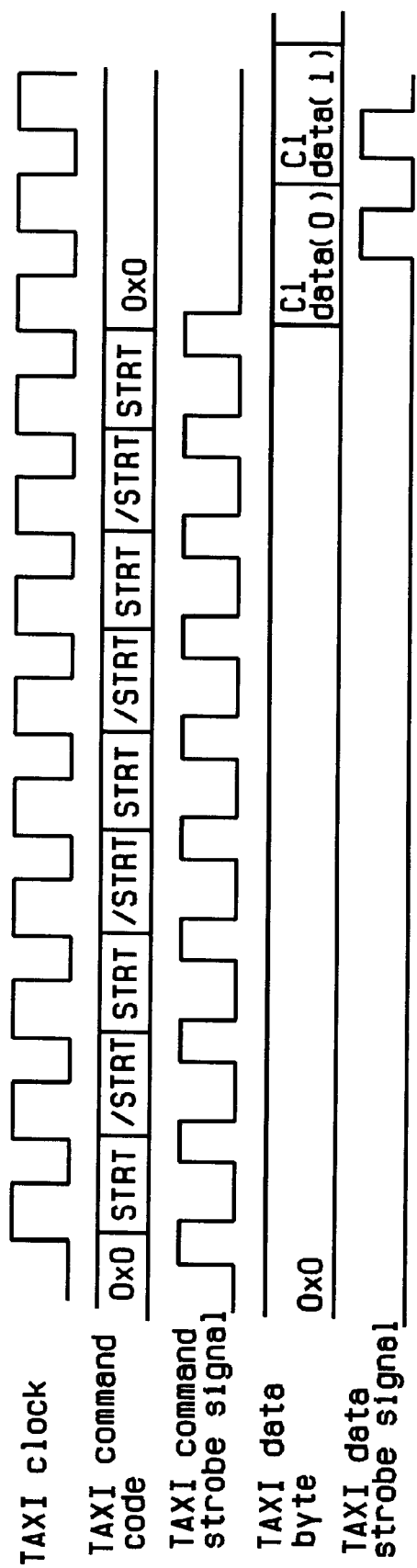
FIG. 8 is a view start detection waveform in of the imaging system shown in FIG. 2.

Transmitter 184 and receiver 204 each include a view start detection algorithm. The view start detection algorithm is necessary because receiver 204 is configured to continuously listen for, or receive, data. After completing the transmission of a selected number of data bytes, transmitter 200 transmits the SYNC sequence to receiver 202. Utilizing the SYNC sequence, receiver 202 remains synchronized to transmitter 200. More specifically, the view start detection algorithm in transmitter 184, transmits a selected TAXI command sequence, or code, repeated a selected number of times, to receiver 204 so that receiver 204 is notified that the next transmitted encoded data is the start of message data. The view start detection algorithm prevents a noise event from causing receiver 204 to improperly decode the incoming noise signal into a data byte. The view start detection algorithm, in one embodiment as shown in FIG. 8, is configured to be tolerant to noise events that are less than or equal to 6 byte clock cycles.

In operation, the intensity signals of detector array 16 are converted using DAS 42. Imaging data are then transmitted from transmitter 114 across slip-ring 116 to receiver 140. More specifically, utilizing the CRC algorithm and the view start detection algorithm, encoded data views are transmitted to receiver 140. After receiver 202 receives a selected number bits, for example 10 bits, from transmitter 200, the bits are evaluated to determine whether the bits could have been generated by TAXI transmitter 200. If determined that the bit code could have been generated by transmitter 200, the bit pattern is decoded by receiver 202 into either a command or an data byte. The command or data byte is then transmitted to data receiver 204 to be checked by the FEC algorithm. If the received bit pattern is incorrect, or corrupt, i.e., the byte decoded by receiver 202 is not the same as the encoded byte sent by transmitter 200, receiver 204 detects and corrects the error.

More specifically, if the bit pattern, received by receiver 202, is determined to be not one generated by transmitter 200, receiver 202 transmits a null data pattern to the CRC algorithm and notifies receiver 204 of the incorrect bit pattern (called a TAXI violation). Within receiver 204, the null data is determined to be incorrect and utilizing the CRC encoding/decoding algorithm the data is corrected. If the transmitted bit pattern is determined to be a SYNC pattern, the count-to-ten counter of receiver 202 is reset and receiver 202 begins looking for valid 10-bit patterns.

The above described imaging system utilizes a communication circuit to transmits high-speed data across an slip-ring without requiring the transmission of an acknowledgment from the receiver to the transmitter. In addition, the communication circuit corrects data errors without re-transmitting the data.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a fill-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required. Accordingly, the spirit and scope of the invention are to be limited only by the terms of the appended claims.

What is claimed is:

1. A method of exchanging data in an imaging system, the imaging system including a view memory, a transmitter configured to generate encoded imaging data, a receiver configured to decode and correct the encoded imaging data, and a RF slip-ring for exchanging the encoded imaging data between a rotating gantry portion and a fixed gantry portion, said method comprising the steps of:

generating encoded message blocks from the view memory using the transmitter;

generating view start commands using the transmitter;

multiplexing the view start commands and the encoded message blocks with SYNC data to generate encoded imaging data;

transmitting the encoded imaging data from the transmitter to the receiver using the slip-ring;

using the SYNC data to synchronize receiver decoding of the encoded imaging data;

decoding the encoded imaging data using the receiver and the view start commands to generate decoded message blocks; and correcting errors in the decoded message blocks using the receiver.

2. A method in accordance with claim 1 wherein transmitting the encoded imaging data comprises the step of asynchronously transmitting the encoded imaging data from the transmitter to the receiver.

3. A method in accordance with claim 1 wherein generating the view start commands comprises the steps of:

generating a group of command codes.

4. A method in accordance with claim 3 further comprising the step of generating zero message blocks.

5. A method in accordance with claim 4 wherein using the SYNC data to synchronize receiver decoding of the encoded imaging data comprises the step of stopping receiving of data by the receiver at intervals defined by a selected number of bytes to identify the SYNC data in the encoded imaging data.

6. A method in accordance with claim 4 wherein decoding the view start commands comprises the steps of:

decoding the command codes.

7. A method in accordance with claim 6 wherein generating the encoded message blocks comprises the step of generating CRC data using the transmitter, and wherein decoding the encoded message blocks comprises the step of decoding the transmitter-generated CRC data using the receiver.

8. A method in accordance with claim 7 wherein correcting errors in the decoded message blocks comprises the steps of:

generating CRC data using the receiver;

determining if the receiver-generated CRC data equals the received, transmitter-generated CRC data.

9. A method in accordance with claim 3 wherein generating the encoded message blocks comprises the step of generating CRC data.

10. A method in accordance with claim 9 wherein encoded message block length is 136 bytes plus a CRC length of 15 bytes.

11. A method in accordance with claim 1 further comprising the step of selecting an error correction code to correct burst errors having durations up to 300 nanoseconds, and wherein said error correction code is utilized to correct the errors in the decoded message blocks.

12. A method in accordance with claim 11 wherein said error correcting code is selected to correct burst errors recurring up to every 25 microseconds.

13. A method in accordance with claim 1 further comprising the step of selecting an error correction code to correct burst errors having durations up to 550 nanoseconds, and wherein said error correction code is utilized to correct the errors in the decoded message blocks.

14. A method in accordance with claim 13 wherein said error correcting code is selected to correct burst error recurring up to every 15 microseconds.

15. An imaging system for scanning an object comprising a view memory, a transmitter configured to generate encoded imaging data, a receiver configured to decode and correct said encoded imaging data, and a RF slip-ring coupled to said transmitter and said receiver for exchanging said encoded imaging data between a rotating gantry portion and a fixed gantry portion, said system configured to:

generate encoded message blocks from the view memory using said transmitter;

generate view start commands using the transmitter;

multiplex the view start commands and the encoded message blocks with SYNC data to generate encoded imaging data;

transmit said encoded imaging data from said transmitter to said receiver using said slip-ring;

use the SYNC data to synchronize receiver decoding of the encoded imaging data;

decode said encoded imaging data using said receiver and the view start commands to generate decoded message blocks; and correct errors in said decoded message blocks using said receiver.

16. A system in accordance with claim 11 wherein transmitting said encoded imaging data, said system configured to asynchronously transmitting said encoded imaging data from said transmitter to said receiver.

17. A system in accordance with claim 15 wherein to generate said view start commands, said system configured to:

generate a group of command codes.

18. A system in accordance with claim 16 further configured to generate zero message blocks.

19. A system in accordance with claim 18 wherein to use the SYNC data to synchronize receiver decoding of the encoded imaging data, said system configured to stop receiving of data by the receiver at intervals defined by a selected number of bytes to identify said SYNC data in the encoded imaging data.

20. A system in accordance with claim 17 wherein to decode said view start commands, said system configured to:

decode said command codes.

21. A system in accordance with claim 20 wherein wherein to generate said encoded message blocks, said transmitter configured to generate transmitted CRC data, and wherein to decode said message blocks, said receiver configured to decode said transmitted CRC data.

22. A system in accordance with claim 21 wherein to correct said errors in said decoded message blocks, said receiver configured to:

generate CRC data;

determine whether said reveiver-generated CRC data equals said received, transmitter-generated CRC data.

23. A system in accordance with claim 17 wherein to generate said encoded message blocks, said system configured to generate CRC data.

24. A system in accordance with claim 23 wherein said message block length is 136 bytes plus a CRC length of 15 bytes.

25. A system in accordance with claim 15 wherein to correct errors in said decoded message blocks, said system is configured to utilize an error correcting code selected to correct burst errors having durations up to 300 nanoseconds.

26. A system in accordance with claim 25 wherein said error correcting code is also selected to correct burst errors recurring up to every 25 microseconds.

27. A system in accordance with claim 15 wherein to correct errors in said decoded message blocks, said system is configured to utilize an error correcting code selected to correct burst errors having durations up to 550 nanoseconds.

28. A system in accordance with claim 27 wherein said error correcting code is also selected to correct burst errors recurring up to every 15 microseconds.

* * * * *

UNITED STATES PATENT AND TRADEMARK OFFICE
CERTIFICATE OF CORRECTION

PATENT NO.    : 6,292,919 B1
DATED         : September 18, 2001
INVENTOR(S)   : Mark David Fries et al.

It is certified that error appears in the above-identified patent and that said Letters Patent is hereby corrected as shown below:

<u>Title page,</u>
Item [57], ABSTRACT,
Line 8, delete "commands" and insert therefore -- command --.

<u>Column 1,</u>
Line 8, after "system" insert therefor -- . --.
Line 59, between "provide" and "communication" insert therefor -- a --.
Line 60, delete "transmit" and insert therefore -- transmits --.

<u>Column 2,</u>
Line 41, delete "a" and insert therefore -- an --.
Line 42, delete "in".

<u>Column 4,</u>
Line 55, delete "disable" and insert therefore -- disabled --.

<u>Column 5,</u>
Lines 58 and 63, delete "stationery" and insert therefore -- stationary --.

<u>Column 7,</u>
Line 4, delete "of".

<u>Column 8,</u>
Lines 25 and 42, delete "an" and insert therefore -- a --.
Line 42, delete "transmits" and insert therefore -- transmit --.
Line 56, delete "fill-" and insert therefore -- full- --.

UNITED STATES PATENT AND TRADEMARK OFFICE
CERTIFICATE OF CORRECTION

PATENT NO.   : 6,292,919 B1
DATED        : September 18, 2001
INVENTOR(S)  : Mark David Fries et al.

It is certified that error appears in the above-identified patent and that said Letters Patent is hereby corrected as shown below:

<u>Column 10,</u>
Line 30, delete "11" and insert therefore -- 15 --.
Line 32, delete "transmitting" and insert therefore -- transmit --.
Line 38, delete "16" and insert therefore -- 17 --.
Line 46, delete "17" and insert therefore -- 18 --.
Line 50, delete "wherein".
Line 60, delete "reveiver" and insert therefore -- receiver --.

Signed and Sealed this

Twelfth Day of August, 2003

JAMES E. ROGAN
*Director of the United States Patent and Trademark Office*